United States Patent [19]
Hood

[11] Patent Number: 6,103,241
[45] Date of Patent: Aug. 15, 2000

[54] ESSENTIAL OIL AND METHODS OF USE

[76] Inventor: John James David Hood, Ducane Waterhouse, Tasmania 7262, Australia

[21] Appl. No.: 09/284,427
[22] PCT Filed: Oct. 20, 1997
[86] PCT No.: PCT/AU97/00701
    § 371 Date: Apr. 26, 1999
    § 102(e) Date: Apr. 26, 1999
[87] PCT Pub. No.: WO98/17749
    PCT Pub. Date: Apr. 30, 1998

[30] Foreign Application Priority Data

Oct. 23, 1996 [AU] Australia .................................. PO3167

[51] Int. Cl.[7] .............................. A61K 35/78; C11B 9/00
[52] U.S. Cl. ............................................................. 424/195.1
[58] Field of Search ........................................... 424/195.1

[56] References Cited

U.S. PATENT DOCUMENTS 4,154,823  5/1979  Schutt ....................... 424/195

OTHER PUBLICATIONS

Lis–Balchin et al. (Acta Horticulturae, No. 426, pp. 13–30), Aug. 1995.

Douglas et al. (Horticulture in New Zealand, vol. 5, No. 2, pp. 22–25), 1994.

"Proceedings of the Essential Oils Planning Workshop," Jun.14–15 1995, Hobart, published by Rural Industries Research and Development Corporation, RIRDC Occasional Paper No. 96/1, pp. 4–17.

*Primary Examiner*—Francisco Prats
*Assistant Examiner*—Susan D. Coe
*Attorney, Agent, or Firm*—Edwin D. Schindler

[57] ABSTRACT

The invention relates to the Essential Oil of the shrub *Kunzea Ambigua* and two various therapeutic uses of the Essential Oil either alone or in carriers and other uses of the Essential Oil.

12 Claims, No Drawings

ESSENTIAL OIL AND METHODS OF USE

ESSENTIAL OIL AND METHODS OF USE

This invention relates to an essential oil and methods of use. Historically, essential oils have been used for medicinal and preservative purposes, and during the Middle Ages, were the basis of basically all pharmaceuticals.

Essential oils, generally, are obtained from the fruit, flower, leaves, bark and wood of plants and can be extracted in a number of ways, often by distillation, either by steam or under vacuum, or by cold pressing.

The object of the present invention is to provide a new essential oil which has beneficial properties.

The invention in its broadest sense includes an essential oil derived from plants of the genus Kunzea.

More specifically, it relates to the essential oil derived from the shrub *Kunzea ambigua*.

The essential oil is adapted for treatment of ailments of the human body, and is applied topically to relieve pain, minimize bruising and to assist in healing, and may be used either pure or in a carrier.

In order that the invention may be more readily understood, I shall describe one particular embodiment of it.

The shrub from which the oil is obtained, a member of the Myrtaceae family, genus Kunzea, species *ambigua*.

The shrub does not appear to be widely distributed, but is found in Tasmania, close to the 41st parallel, in a cool, temperate climate with a rainfall of the order of 850 millimeters.

The shrub is hardy and can be harvested by being topped mechanically with a forage harvester.

The harvester thus retrieves the leaves, small stems and seed bolls.

Because the plant is hardy, there will be substantial regrowth, and it is possible to re-harvest the plant after one or two years.

The material harvested is placed in a still and steam distillation is used to break down the cells of the plant to release the oil, and the oil is carried over with the steam, which is condensed and the oil/water so formed is passed into a container where the oil floats to the top and can be drained off.

The attached examples show the results of gas chromatograph analysis of the oil made from the shrub, and it will be seen that its principal components in each example are mono- and sesqui-terpenes.

Considering Example 1, the largest components are α pinene, 50.52 percent, 1-8-cineole, 14.08 percent, and sesquiterpene alcohols, globulol, 6.81 percent, and viridiflorol, 5.96 percent.

In Example 2, again the largest components are α pinene, 41.5 percent, 1-8-cineole, 12.1 percent and in this case, there are identified 3 sesquiterpene alcohols which together are 25.5 percent.

Whilst other analyses of the oils have varied in absolute percentage, the relative percentages of the various components are very similar, with a preponderance of the above components.

I have had trials done with the oil in a number of therapeutic applications, and although full trials has not been completed, I have found, qualitatively, that the oil has the ability to reduce pain caused by muscle and tendon strain and impact trauma, and it has also been found to reduce pain from gout, headache and bites, particularly insect and spider bites.

It has also had positive results in the treatment of rashes, skin irritations and acne.

It also seems to provide a positive result in relieving sinus congestion and as a result of this, aids in the return of the senses of smell and taste.

It also appears to have an ability to prevent the progress of cold sores, although to date the results in treating genital herpes have not been so positive.

One area which has provided a surprising reaction is in the treatment of bruising.

If applied to the area after the trauma and before bruising has started or is only incipient, I have found that it is almost completely ameliorated.

The oil appears to have no strongly adverse reaction with the skin, although as with all essential oils, people with sensitive skin should be careful before they apply it at full strength, but it can readily be applied, diluted in a carrier oil, preferably a pure vegetable oil, a lotion which can be an aqueous suspension, or an ointment, which can often be a petroleum emulsifying ointment base.

Where the *Kunzea ambigua* oil is applied, either pure or in a carrier oil or a lotion, the oil seems to pass through the skin relatively quickly, so no doubt it has a molecular size to enable this to occur, although to date I have not studied the size of the molecule.

The *Kunzea ambigua* shrub apparently is distasteful to sheep, and they will not eat this, so it means that the shrub can be left with or planted together with pasture and sheep will not damage the shrub, but will eat the pasture, and so effectively keep the area generally clean. This means that where the shrub is grown for oil production, one can get effectively a twin use of the land.

Also, it may well be that some selective propagation can be used to maximise the return from the shrub when harvested, but to date I have not had an opportunity to do this.

Apart from its pharmaceutical benefits, the oil can be used in other ways.

Firstly, it can be used in an oil disseminator. The smell is refreshing and not unduly objectionable. Also, it may well be useful in a perfume as a perfume base, and it also could readily be added to skin care products so that the benefit of the oil is achieved by the normal day by day use of the product.

I have found that the oil acts as a very good rust inhibitor, one of the indicators which led to the oil was that fence wires in close proximity to the shrub in an area with a high salt content did not rust as expected, and it is believed that it was evaporation of the oil from the leaves of the shrub which caused this.

Also, the oil can be used in craft work for polishing timber or the like, the timber so polished not only having a good appearance, but also the residual smell of the oil.

Whilst I have described the oil itself, its method of production and various uses, it is to be understood that these may be developed as the use of the oil continues.

Whilst in the above embodiment, I have described the use of the oil derived from the shrub *Kunzea ambigua*, it is believed that the oils derived from other plants of the genus Kunzea may have similar properties.

EXAMPLE 1

| Sample | GC# | Pk# | Component Identified | % of total area (FID) |
|---|---|---|---|---|
| EOT 671 | 3110 | 1 | α-pinene | 50.52 |
| | | 2 | β-pinene | 0.54 |
| | | 3 | sabiene | 0.49 |
| | | 4 | myrcene | 0.36 |
| | | 5 | limonene | 1.24 |
| | | 6 | 1-8-cineole | 14.08 |
| | | 7 | γ-terpinene | trace |
| | | 8 | trans-β-ocimene | 0.65 |
| | | 9 | P-cymene | 0.36 |
| | | 10 | 3-methyl butyl isovalerate (iso amyl isovalerate) | 0.61 |
| | | 11 | terpine-4-ol + caryophyllene | 1.43 |
| | | 12 | α-terpineol | 2.25 |
| | | 13 | bicyclogermacrene | 4.11 |
| | | 14 | calamenene | 1.14 |
| | | 15 | globulol | 6.81 |
| | | 16 | viridifloral | 5.95 |
| | | 17 | spathulenol | 0–82 |
| | | | Other unidentified Identified components | 8.71 |

Parsley Oil Blend (ex Traatt=returned)

| Sample | GC # | α-pinene | β-pinene | % menthatriene | % TMAB | % elemicin | % myristicin | % apicie |
|---|---|---|---|---|---|---|---|---|
| EOT 664 | 3106 | 17.25 | 12.07 | 22.86 | 2.97 | 1.15 | 19.02 | 0.69 |

GC FID comparative analysis (against fennel+peppermint standards) and GCMS analysis failed to detect any menthol or anethole (etc) contaminants.

EXAMPLE 2

| COMPOUND | Percentage or TIC area | COMPOUND | Percentage or TIC area |
|---|---|---|---|
| Alpha-Pinene | 41.5 | Alpha-Terpineol | 1.5 |
| Sabinene | 0.7 | Citronellol | 0.7 |
| Beta-Pinene | 0.5 | Alpha-Gurjunene | 0.3 |
| Myrcene | 0.3 | Caryophyllene | 0.7 |
| Alpha-Terpinene | 0.15 | Bicyclogermacrene | 6.4 |
| P-Cyrnene | 0.3 | Calamenene | 0.8 |
| 1,8-Cineole | 12.1 | Delta-Cadinene | 0.3 |
| Limonene | 1.2 | Palustrol | 0.5 |
| Beta-Ocimene | 0.3 | Spathulenol | 0.7 |
| Gamma-Terpinene | 0.3 | 'Sesquiterpene Alcohol 1' | 11.8 |
| Terpinolene | 0.1 | 'Sesquiterpene Alcohol 2' | 11.9 |
| Linalool | 0.2 | 'Sesquiterpene Alcohol 3' | 1.8 |
| Isoamyl Isovalerate | 0.6 | Terpinene-4-ol | 0.2 |

What is claimed is:

1. An essential oil extracted from a scrub of the genus and species *Kunzea ambigua*.

2. The essential oil according to claim 1, wherein said essential oil is extracted via a distillation of said shrub.

3. The essential oil according to claim 2, wherein the distillation is steam distillation.

4. The essential oil according to claim 1, wherein said essential oil comprises alpha-pinene, 1,8-cineole and, at least, one sesquiterpene alcohol.

5. A method for reducing pain, controlling bruising and aiding in a healing of skin, said method comprising the steps of:
 extracting an essential oil from a shrub of the genus and species *Kunzea ambigua*; and,
 topically applying to a person's skin said essential oil.

6. The method according to claim 5, wherein said essential oil is extracted via a distillation of said shrub.

7. The method according to claim 6, wherein the distillation is steam distillation.

8. The method according to claim 5, wherein said essential oil comprises alpha-pinene, 1,8-cineole and, at least, one sesquiterpene alcohol.

9. The method according to claim 5, further comprising the step of mixing said essential oil with a carrier substance, prior to said topically applying step.

10. The method according to claim 9, wherein said carrier substance is a vegetable oil.

11. The method according to claim 9, wherein said carrier substance is a lotion.

12. The method according to claim 9, wherein said carrier substance is an ointment.

* * * * *